United States Patent [19]

Cipolli et al.

[11] Patent Number: 5,371,218

[45] Date of Patent: Dec. 6, 1994

[54] SALTS OF TRIAZINE COMPOUNDS WITH CYANURIC ACID

[75] Inventors: Roberto Cipolli, Novara; Roberto Oriani, Milan; Gilberto Nucida, San Giuliano Milanese; Enrico Masarati, Castelnuovo Valtidone, all of Italy

[73] Assignee: Ministero Dell'Universita' e Della Ricerca Scientifica, Rome, Italy

[21] Appl. No.: 984,106

[22] Filed: Dec. 1, 1992

[30] Foreign Application Priority Data

Dec. 4, 1991 [IT] Italy ............. MI91 A 003252

[51] Int. Cl.$^5$ ............................. C07D 403/14
[52] U.S. Cl. ................................. 544/198
[58] Field of Search ............ 544/192, 193.2, 198

[56] References Cited

U.S. PATENT DOCUMENTS

| 4,249,004 | 2/1981 | Chono et al. | 544/192 |
| 4,567,259 | 1/1986 | Sawa et al. | 544/207 |
| 4,574,154 | 3/1986 | Okamoto et al. | 544/192 |
| 4,727,102 | 2/1988 | Scarso | 524/100 |
| 5,202,438 | 4/1993 | Paul | 544/198 |

FOREIGN PATENT DOCUMENTS 0406810 1/1991 European Pat. Off. .
0466137 1/1992 European Pat. Off. .

OTHER PUBLICATIONS

Chemical Abstracts, vol. 85, 1976, No. 95212n, T. Tsutsumi, et al., "Flame-Resistant Polyamide Compositions".

Chemical Abstracts, vol. 113, 1990, No. 175187y, Z. Wen, "Manufacture and Application of Melamine Cyanuric Acid–Flame Retardant Lubricant Agent".

*Primary Examiner*—Mukund J. Shah
*Assistant Examiner*—P. K. Sripada
*Attorney, Agent, or Firm*—Oblon, Spivak, McClelland, Maier & Neustadt

[57] ABSTRACT

Salts of triazine compounds with cyanuric acid, of general formula (I):

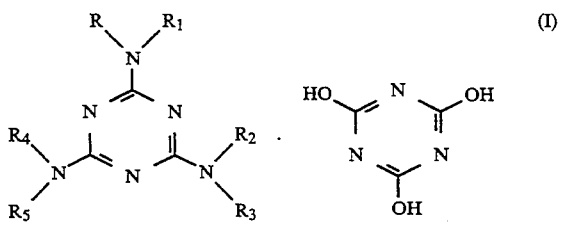

obtained by salifying 2,4,6-triamino-1,3,5-triazine derivatives with cyanuric acid. The new salts of general formula (I) are used in particular as flame retardant additives.

3 Claims, No Drawings

SALTS OF TRIAZINE COMPOUNDS WITH CYANURIC ACID

This invention relates to salts of triazine compounds with cyanuric acid.

More particularly, the invention relates to salts of 2,4,6-triamino-1,3,5-triazine derivatives with cyanuric acid. These compounds are used in the preparation of self-extinguishing polymeric compositions based on thermoplastic polymers or polymers with elastomeric properties, especially olefinic polymers or copolymers, in combination with ammonium or amine phosphates and/or phosphonates.

2,4,6-triamino-1,3,5-triazine derivatives are known from European patent 406,810 as flame retardant additives. However these additives have poor thermal stability, expressed as weight loss with increasing temperature (T.G.A.).

The applicant has now found that the salts of the present invention not only possess unaltered flame-retardant characteristics but also show excellent stability towards heat. Specifically, the present invention provides the salts of general formula (I):

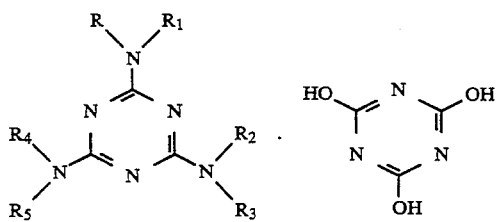

where:
at least one of the radicals from R to $R_5$ is:

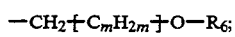

$$-CH_2 \!-\! (C_mH_{2m}) \!-\! O \!-\! R_6;$$

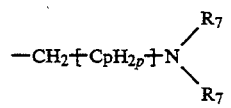

in which:
m is a whole number between 1 and 7:
p is a whole number between 1 and 5:
$R_6$ is H; $C_1$–$C_8$ alkyl $C_2$–$C_6$ alkenyl; —[$C_qH_{2q}$]O—$R_8$ where q is a whole number between 1 and 4 and $R_8$ is H or $C_1$–$C_4$ alkyl; $C_6$–$C_{12}$ cycloalkyl or alkylcycloalkyl;
the radicals $R_7$, which can be the same or different, are: H; $C_1$–$C_8$ alkyl; $C_2$–$C_6$ alkenyl; $C_6$–$C_{12}$ cycloalkyl or alkylcycloalkyl; $C_1$–$C_4$ hydroxyalkyl; or the group:

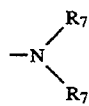

is replaced by a heterocyclic radical bound to the alkyl chain by the nitrogen atom and possibly containing a further heteroatom chosen preferably from O, S and N; or in general formula (I) at least one of the groups:

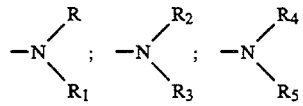

is replaced by a heterocyclic radical bound to the triazine ring by the nitrogen atom and possibly containing a further heteroatom chosen preferably from O, S and N.

The other radicals from R to $R_5$, which can be the same or different, have the aforesaid meaning or are: H; $C_1$–$C_{18}$ alkyl; $C_2$–$C_8$ alkenyl; $C_6$–$C_{16}$ cycloalkyl or alkylcycloalkyl, possibly substituted with a hydroxyl or $C_1$–$C_4$ hydroxyalkyl function.

Examples of radicals from R to $R_5$ in general formula (I) are: methyl, ethyl, propyl, isopropyl, n-butyl, isobutyl, tert-butyl, n-pentyl; isopentyl; n-hexyl; tert-hexyl; octyl; tert-octyl; decyl; dodecyl; octadecyl; ethenyl; propenyl; butenyl; isobutenyl; hexenyl; octenyl; cyclohexyl; propylcyclohexyl; butylcyclohexyl; decylcyclohexyl; hydroxycyclohexyl; hydroxyethylcyclohexyl; 2-hydroxyethyl; 2-hydroxypropyl; 3-hydroxypropyl; 3-hydroxybutyl; 4-hydroxybutyl; 3-hydroxypentyl; 5-hydroxypentyl; 6-hydroxyethyl; 3-hydroxy-2,5-dimethylhexyl; 7-hydroxyheptyl; 7-hydroxyoctyl; 2-methoxyethyl; 2-methoxypropyl; 3-methoxypropyl; 4-methoxybutyl; 6-methoxyethyl; 7-methoxyheptyl; 7-methoxyoctyl; 2-ethoxyethyl; 3-ethoxypropyl; 4-ethoxybutyl; 3-propoxypropyl; 3-butoxypropyl; 4-butoxybutyl; 4-isobutoxybutyl; 5-propoxypentyl; 2-cyclohexyloxyethyl; 2-ethenyloxyethyl; 2-(N,N-dimethylamino)ethyl; 3-((N,N-dimethylamino)propyl; 4-(N,N-dimethylamino)butyl; 5-(N,N-dimethylamino)pentyl; 4-(N,N-diethylamino)butyl; 5-(N,N-diethylamino) pentyl; 5-(N,N-diisopropylamino)pentyl; 3-(N-ethylamino)propyl; 4-(N-methylamino)butyl; 4-(N,N-dipropylamino)butyl; 2-(N,N-diisopropylamino)ethyl; 6-(N-hexenylamino)hexyl; 2-(N-ethenylamino) ethyl; 2-(N-cyclohexylamino)ethyl; 2-(N-2-hydroxyethylamino)ethyl; 2-(2-hydroxyethoxy)ethyl; 2-(2-methoxyethoxy)ethyl; 6-(N-propylamino)hexyl; and so forth.

Examples of heterocyclic radicals which can replace the groups:

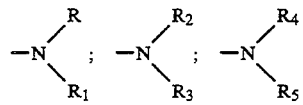

in general formula (I) are: aziridine; pyrrolidine; piperidine: morpholine; thiomorpholine; piperazine; 4-methylpiperazine; 4-ethylpiperazine 2-methylpiperazine; 2,5-dimethylpiperazine; 2,3,5,6-tetramethylpiperazine; 2,2,5,5-tetramethylpiperazine; 2-ethylpiperazine; 2,5-diethylpiperazine; and so forth.

Examples of heterocyclic radicals which can replace the group:

are: aziridine; pyrrolidine piperidine; morpholine; thiomorpholine; piperazine: 4-methylpiperazine; 4-ethylpiperazine; and so forth. Specific compounds included in formula (I) are given in the examples which follow this description.

The saline products of general formula (I) can be synthesized by reacting one mole of the 2,4,6-triamino-1,3,5-triazine derivative of general formula (II):

(II)

presence of a suitable solvent (such as water, methyl alcohol, ethyl alcohol, acetonitrile, and so forth at a temperature between 0° C. and the boiling point of the solvent used.

The saline product formed can be easily separated from the reaction mass by filtration or by distilling the solvent. Generally, good quality products of general formula (I) are obtained in the form of a white crystalline powder usable in a self-extinguishing polymeric compositions without further purification.

Many of the intermediates of general formula (II) are known, and can be easily synthesized by the general method shown schematically below:

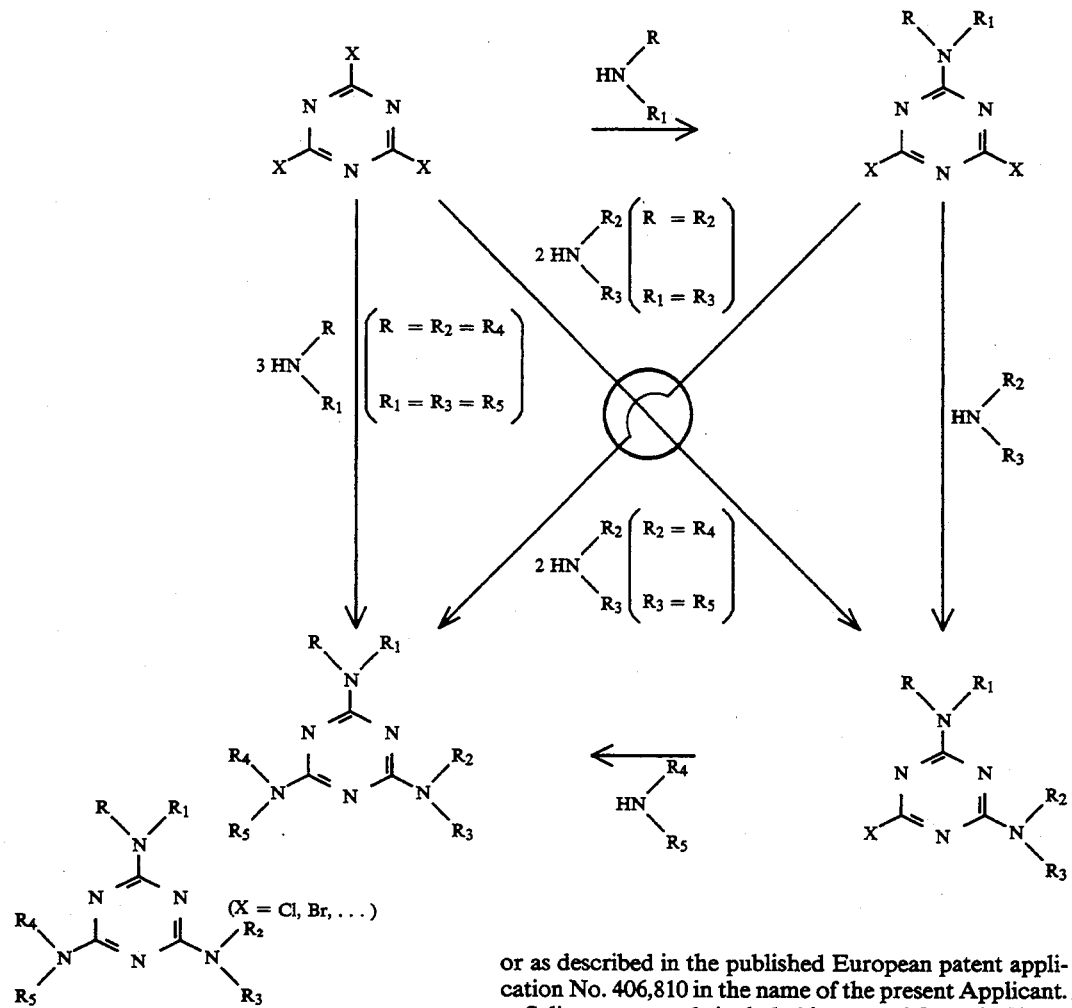

where the substituents from R to $R_5$ have the aforedefined meaning, with one mole of cyanuric acid in the or as described in the published European patent application No. 406,810 in the name of the present Applicant.

Saline compounds included in general formula (I) but not cited in the examples are shown in Table 1.

TABLE 1

| Compound No. | $R-N-R_1$ | | $R_2-N-R_3$ | | $R_4-N-R_5$ | |
|---|---|---|---|---|---|---|
| 1 | $(CH_2)_2OCH=CH_2$ | H | H | H | H | H |
| 2 | $\overset{N\phantom{xxx}N-CH_3}{\frown\!\!\smile}$ | | $CH_2CH_2OCH_3$ | H | H | H |
| 3 | $CH_2CH_2CH_2N\overset{\frown}{\underset{\smile}{\phantom{xx}}}O$ | H | H | H | H | H |

TABLE 1-continued

| Compound No. | R—N—R$_1$ | | R$_2$—N—R$_3$ | | R$_4$—N—R$_5$ | |
| --- | --- | --- | --- | --- | --- | --- |
| 4 | morpholino (N-O ring) | | t-C$_4$H$_9$ | H | H | H |
| 5 | (CH$_2$)$_2$O(CH$_2$)$_2$OH | H | (CH$_2$)$_2$O(CH$_2$)$_2$OH | H | H | H |
| 6 | CH$_2$CH$_2$OH | | cyclohexyl | H | H | H |
| 7 | thiomorpholino (N-S ring) | | CH$_2$CH$_2$OH | H | H | H |
| 8 | CH$_2$CH$_2$OH | | CH$_2$CH$_2$OH | H | H | H |
| 9 | morpholino (N-O ring) | | t-C$_8$H$_{17}$ | H | H | H |
| 10 | (CH$_2$)$_5$OH | H | H | H | H | H |
| 11 | N-methylpiperazino (N N—CH$_3$ ring) | | H | H | H | H |
| 12 | piperidino (N ring) | | H | H | H | H |
| 13 | (CH$_2$)$_4$OCH$_3$ | H | H | H | H | H |
| 14 | CH$_2$CHOH\|CH$_3$ | H | CH$_2$CHOH\|CH$_3$ | H | H | H |
| 15 | (CH$_2$)$_3$N(C$_2$H$_5$)$_2$ | H | H | H | H | H |
| 16 | (CH$_2$)$_2$OCH=CH$_2$ | CH$_3$ | H | H | H | H |
| 17 | CH$_2$CH$_2$OH | H | CH$_2$CH$_2$OH | H | CH$_2$CH$_2$OH | H |
| 18 | azetidino (N ring) | | H | H | H | H |
| 19 | (CH$_2$)$_3$OC$_2$H$_5$ | H | H | H | H | H |
| 20 | CH$_2$CH$_2$OH | CH$_3$ | CH$_2$CH$_2$OH | CH$_3$ | H | H |
| 21 | (CH$_2$)$_3$OCH$_3$ | H | (CH$_2$)$_3$OCH$_3$ | H | (CH$_2$)$_3$OCH$_3$ | H |
| 22 | morpholino (N-O ring) | | CH$_2$CH$_2$OCH$_3$ | H | CH$_2$CH$_2$OCH$_3$ | H |

The following examples illustrate but do not limit the characteristics of the invention.

The salification reactions between the intermediates of general formula (II) and the cyanuric acid are confirmed by IR spectroscopic analysis on a Perkin Elmer 580B grid spectrophotometer.

It was found that the band relative to deformation outside the plane of the triazine fine formed an excellent reference signal. This lies at about 830–800 cm$^{-1}$ for the undisturbed ring, whereas it lies at 795–760 cm$^{-1}$ for the ring salified on amino groups.

EXAMPLE 1

184.5 g of cyanuric chloride and 800 cm$^3$ of acetone are fed into a 3 liter reactor fitted with a stirrer, thermometer, dropping funnel, reflux condenser and heating bath.

The mixture is heated to 40° C. and stirred until a solution is obtained, after which 284 g of a 30 wt % aqueous ammonia solution are added over a period of 1 hour 30 minutes while maintaining the temperature at 40° C. The solution is then heated to 45° C. and maintained at this temperature for 4 hours.

After cooling, the product which forms is filtered off and washed with water on the filter.

After drying in an oven at 50°–60° C. under vacuum. 113 g of the intermediate (III):

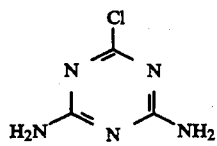

are obtained in the form of infusible white crystalline powder with a chlorine content of 24.12% (theoretical=24.36%). 101.9 g of the intermediate (III), 500 cm³ of water and, under agitation. 44.8 g of 2-hydroxyethylamine are fed into a 1 liter reactor fitted with stirrer, thermometer, dropping funnel, reflux condenser and heating bath.

The mixture is heated to boiling and maintained under reflux for 4 hours.

It is then further left under reflux for 8 hours while adding 29 g of sodium hydroxide dissolved in 90 cm³ of water in such portions as to maintain the pH between 7 and 8.

It is cooled to 15° C. and the product which forms is filtered off, then washed on the filter with cold water.

On drying the filter cake in an oven at 100° C. 107.5 g of 2-(2-hydroxyethyl)amino-4,6-diamino-1,3,5-triazone (IV):

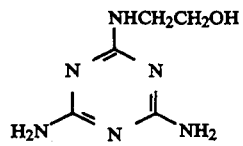

are obtained in the form of a white crystalline powder with m.p.=225°–230° C. (m.p.=melting point).

The structure of the intermediates (III) and (IV) was confirmed by IR spectroscopic analysis.

500 cm³ of water and, under agitation, 68.0 g of the intermediate (IV) and 51.6 g of cyanuric acid are fed into the same 1 liter reactor.

The mass is heated to boiling and maintained under reflux for 10 hours.

It is allowed to cool to room temperature and the product formed is filtered off and washed with water on the filter. On drying the filter cake in an oven at 100° C., 118.4 g of the product:

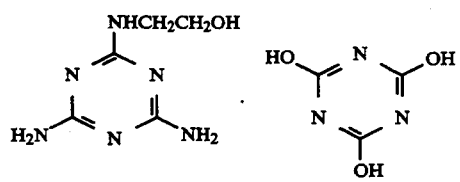

are obtained in the form of a white crystalline powder with m.p. exceeding 300° C.

EXAMPLE 2

600 cm³ of water and 92.2 g of cyanuric chloride are fed into a 2 liter reactor equipped as in Example 1 but initially provided with a cooling bath.

After cooling to 2° C. from the outside, 75.0 g of 2-methoxyethylamine in 100 cm³ of water are fed in over a time of 2 hours. During the addition the temperature is allowed to rise gradually to 5°–7° C.

The temperature is raised to 20° C. and maintained at this value for 1 hour, after which it is raised to 35°–40° C., and 40 g of sodium hydroxide dissolved in 100 cm³ of water are added over about 3 hours.

The reaction mass is heated to 60° C. and this temperature maintained for 2 hours.

It is cooled to room temperature and the product which forms is filtered off and washed on the filter with water.

On drying the filter cake in an oven at 100° C. 120.4 g of the intermediate (V):

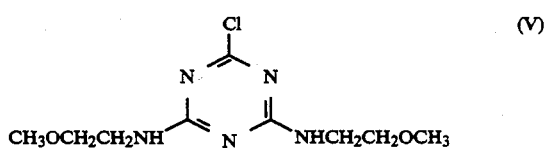

are obtained in the form of a white crystalline powder of m.p.=162°–164° C. with a chlorine content of 13.48% (theoretical=13.57%).

600 cm³ of water, 78.5 g of the intermediate (V) and 22.5 g of 2-methoxyethylamine are fed into the same 2 liter reactor.

The mass is heated to boiling and maintained under reflux for 2 hours, after which 12 g of sodium hydroxide dissolved in 50 cm³ of water are added over about 3 hours.

Boiling is maintained for a further 2 hours, after which it is cooled to room temperature.

The aqueous solution is treated with three 300 cm³ portions of methylene chloride.

The organic extracts are pooled, dried and distilled. 86.7 g of 2,4,6-tris(2-methoxyethyl)amino-1,3,5-triazine (VI):

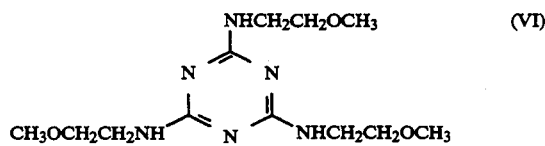

are obtained in the form of a very dense liquid product (m.p.=13° C.).

The structure of the intermediates (V) and (VI) was confirmed by NMR analysis.

400 cm³ of water and, under agitation, 64.4 g of the intermediate (VI) and 19.4 g of cyanuric acid are fed into the same 1 liter apparatus.

The mass is heated to boiling and maintained under reflux for 4 hours.

It is allowed to cool to room temperature and the product formed is filtered off and washed with water on the filter.

On drying the filter cake in an oven at 100° C., 83.2 g of the product:

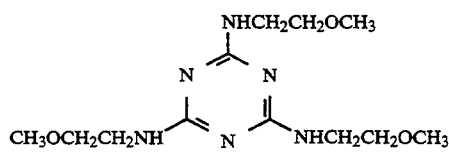 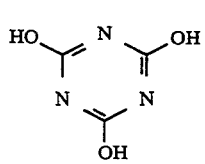

are obtained in the form of a white crystalline powder with its m.p. exceeding 300° C.

EXAMPLE 3

91 g of the intermediate (III), 240 cm³ of toluene and 110 g of morpholine are fed into the 1 liter apparatus described in Example 1.

The mixture is heated to 65°–70° C. and maintained at this temperature for 2 hours. It is then heated to boiling and maintained under reflux for 1 hour.

It is left to cool to room temperature, after which the product is removed by filtration. The filter cake is washed abundantly with water to obtain, after drying, 92 g of 2,4-diamino-6-morpholino-1,3,5-triazine (VII):

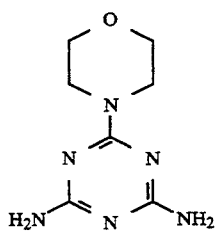 (VII)

in the form of a white crystalline powder with m.p.=248°–250° C.,

The structure of the intermediate (VII) was confirmed by IR spectroscopic analysis.

300 cm³ of water and, under agitation, 39.2 g of the intermediate (VII) and 25.8 g of cyanuric acid are fed into a 0.5 liter reactor equipped as in Example 1.

The mass is heated to boiling and maintained under reflux for 14 hours.

It is then cooled to room temperature and the product formed is filtered off and washed with water.

On drying the filter cake in an oven at 100° C., 64.5 g of the product:

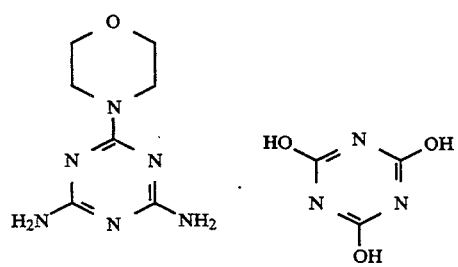

are obtained in the form of a white crystalline powder with m.p. exceeding 300° C.

EXAMPLE 4

136 g of the intermediate (III) and 800 cm³ of xylene are fed into the 3 liter apparatus of Example 1.

The suspension is heated to 120° C. and 302 g of the ethyl ester of N-piperazinecarboxylic acid are added over 1 hour.

The mixture is maintained at 125°–130° C. for 2 hours, after which it is cooled to room temperature and the formed product is filtered off, the filter cake being washed firstly with xylene and then abundantly with water.

After drying in an oven at 100° C., 230 g of the intermediate (VIII):

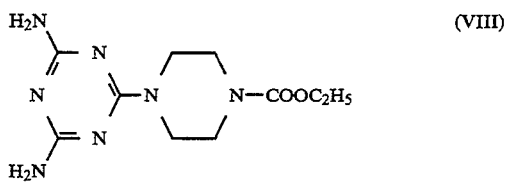 (VIII)

are obtained as a white crystalline powder with m.p.=210°–215° C.

The structure of the intermediate (VIII) was confirmed by NMR analysis.

1000 cm³ of acetic acid, 620 g of a 33 wt % acetic solution of hydrobromic acid and 120 g of the intermediate (VIII) are fed into the same apparatus.

The mixture is heated to 95° C. and maintained under agitation at this temperature for 6 hours.

It is then cooled to room temperature and the formed product is filtered off and washed on the filter with acetic acid.

The squeezed filter cake is taken up in a 2 liter beaker with 500 cm³ of water, and a 50 wt % aqueous sodium hydroxide solution added under agitation until pH 11 is attained.

The mixture is left under agitation for a further 1 hour, after which the formed product is filtered off and washed abundantly on the filter with water.

On drying in an oven at 100° C., 60 g of 2,4-diamino-6-piperazino-1,3,5-triazine (IX):

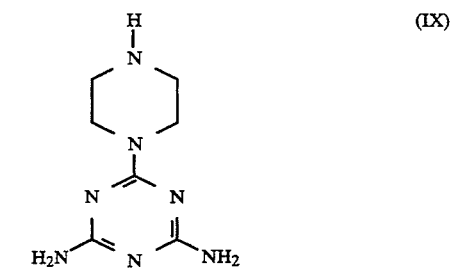 (IX)

are obtained in the form of a white crystalline powder with m.p.=262°–268° C.

The structure of the intermediate (IX) was confirmed by IR spectroscopic analysis.

450 cm³ of water and, under agitation, 48.8 g of the intermediate (IX) and 32.3 g of cyanuric acid are fed into the 1 liter apparatus of Example 1.

The mass is heated to boiling and maintained under reflux for 8 hours.

It is then allowed to cool to room temperature and the product formed is filtered off and washed with water.

On drying the filter cake in an oven at 100° C., 78.6 g of the product:

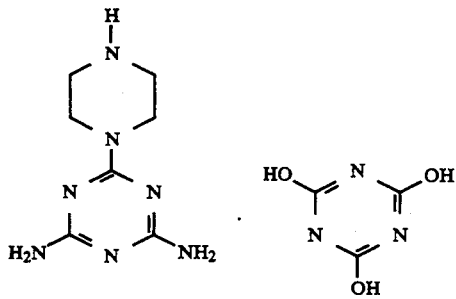

are obtained in the form of a white crystalline powder with m.p. exceeding 300° C.

EXAMPLE 5

184.5 g of cyanuric chloride and 1300 cm³ of methylene chloride are fed into the 3 liter apparatus described in Example 1 but provided initially with a cooling bath.

After cooling from the outside, 87.2 g of morpholine and 40 g of sodium hydroxide dissolved in 150 cm³ of water are fed in simultaneously over 3 hours while maintaining the pH between 5 and 7 and the temperature between 0° and 3° C.

The temperature is maintained at 0°-3° C. for a further 3 hours, after which the aqueous phase is separated.

By distilling the methylene chloride 230 g of the intermediate (x):

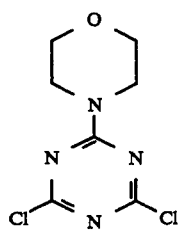

are obtained in the form of a white crystalline powder with m.p.=155°-157° C., at a purity exceeding 98% (determined by gas chromatography) and with a chlorine content of 29.87% (theoretical 30.21%).

100 g of a 30 wt % ammonia solution, 100 cm³ of water and 70.5 g of the intermediate (X) are fed into a 0.5 liter reactor equipped as in Example 1.

The mixture is heated to 50° C. and maintained for 7 hours at this temperature. It is allowed to cool to room temperature, the product obtained is filtered off and washed with water.

On drying the filter cake, 58 g of the intermediate (XI):

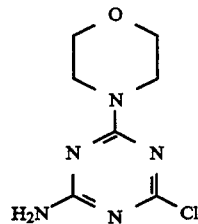

are obtained in the form of a white crystalline powder with m.p.=189°-191° C., with a chlorine content of 16.28% (theoretical 16.47%). 58 g of the intermediate (XI) and 300 cm³ of water are fed into the same apparatus, followed, under agitation, by 18 g of 2-aminoethanol.

The mixture is heated to boiling and maintained under reflux for 3 hours.

It is then further left under reflux for 3 hours while adding 11.8 g of sodium hydroxide dissolved in 50 cm³ of water in such portions as to maintain the pH between 7 and 8.

The mass is cooled, the product filtered off and the filter cake washed with water.

On drying, 58 g of 2-amino-4-(2-hydroxyethyl)amino-6-morpholino-1,3,5-triazine (XII):

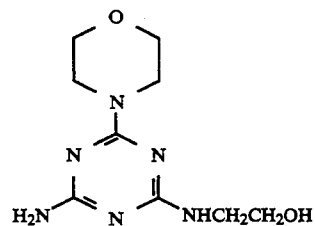

are obtained in the form of a white crystalline powder with m.p.=159°-161° C.

The structure of the intermediates (X), (XI) and (XIII) was confirmed by IR spectroscopic analysis.

450 cm³ of water and, under agitation, 48.0 g of the intermediate (XII) and 25.8 g of cyanuric acid are fed into the 1 liter apparatus of the preceding examples.

The mass is heated to boiling and maintained under reflux for 10 hours.

Proceeding as described in the preceding examples, 72.9 g of the product:

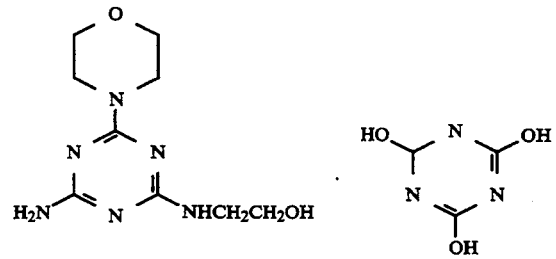

are obtained in the form of a white crystalline powder with m.p.=270°-274° C.

EXAMPLES 6-10

Operating under conditions analogous to those described in Examples from 1 to5, the saline products of general formula (I) shown in Table 2 are prepared.

TABLE 2

| Example No. | R—N—R$_1$ | | R$_2$—N—R$_3$ | | R$_4$—N—R$_5$ | | m.p. (°C.) |
|---|---|---|---|---|---|---|---|
| 6 | morpholino (N—O ring) | | CH$_2$CH=CH$_2$ | H | H | H | 237–240 |
| 7 | CH$_2$CH$_2$OCH$_3$ | H | H | H | H | H | >300 |
| 8 | CH$_2$CH$_2$OCH$_3$ | CH$_2$CH$_2$OCH$_3$ | H | H | H | H | 258–262 |
| 9 | CH$_2$CH$_2$OH | H | CH$_2$CH$_2$OH | H | H | H | 290–295 |
| 10 | thiomorpholino (N—S ring) | | H | H | H | H | >300 |

Table 3 shows the results of thermogravimetric analysis (T.G.A.) of some of the salts of general formula (I) described in the examples of the present invention, compared with those of the corresponding 2,4,6-triamino-1,3,5-triazine derivatives of general formula (II).

The thermal stability of these products was determined by evaluating the weight lost on temperature increase.

A DU PONT Model 951-9900 thermobalance was used, operating with an air rate of 5 liters/hour, a heating rate of 20° C./minute within the temperature range of 20°–600° C., and a product quantity of about 10 mg.

TABLE 3

| Weight loss (%) | Product Example 1 | | Product Example 3 | | Product Example 4 | | Product Example 5 | | Product Example 6 | |
|---|---|---|---|---|---|---|---|---|---|---|
| | (I) | (II) | (I) | (II) | (I) | (II) | (I) | (II) | (I) | (II) |
| 2  | 294 | 267 | 252 | 235 | 255 | 250 | 271 | 242 | 227 | 213 |
| 5  | 313 | 267 | 268 | 252 | 282 | 267 | 287 | 259 | 242 | 226 |
| 10 | 323 | 280 | 283 | 264 | 306 | 280 | 297 | 276 | 262 | 241 |
| 20 | 329 | 298 | 297 | 277 | 319 | 294 | 303 | 294 | 285 | 258 |
| 50 | 396 | 381 | 319 | 301 | 349 | 322 | 374 | 337 | 315 | 286 |

(I) Salt of general formula (I)
(II) 2,4,6-triamino-1,3,5-triazine derivative of general formula (II)

EXAMPLE 11

75.0 g of isotactic polypropylene in flakes with a melt flow index of 12 and a fraction insoluble in boiling n-heptane of 96% by weight, 8.0 g of the product of Example 3, 16.0 g of ammonium polyphosphate (Exolit 422 ® from Hoechst), 0.67 g of dilaurylthiopropionate and 0.33 g of pentaerythritol tetra[3-(3,5-di-tert-butyl-4-hydroxyphenyl)propionate] are mixed together and moulded in a MOORE plate press, operating for 7 minutes at a pressure of 40 kg/cm$^3$.

Test pieces in the form of plates of about 3 mm thickness are obtained, on which the self-extinguishing level is determined by measuring the oxygen index (L.O.I. in accordance with ASTM D-2863/77) in a STANTON REDCROFT apparatus, and applying the "Vertical Burning Test" which makes it possible the material to be classified in three classes, namely 94 V-0, 94 V-1 and 94 V-2 in accordance with the UL 94 standards (published by the Underwriters Laboratories, USA).

The following results are obtained:
L.O.I.=31.4
UL 94: class V-0.

We claim:

1. Salts of triazine compounds with cyanuric acid, of formula (I):

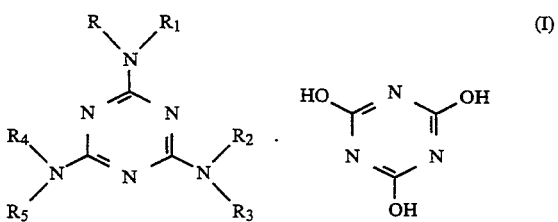

where:

at least one of the radicals from R to R$_5$ is:

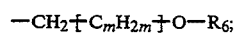

$-CH_2 \text{\textemdash} (C_mH_{2m}) \text{\textemdash} O \text{\textemdash} R_6$;

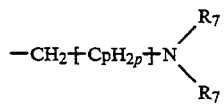

in which:
m is a whole number between 1 and 7;
p is a whole number between 1 and 5;
R$_6$ is H; C$_1$-C$_8$ alkyl; C$_2$-C$_6$ alkenyl; —[C$_q$H$_{2q}$]O—R$_8$ where q is a whole number between 1 and 4 and R$_8$ is H or C$_1$-C$_4$ alkyl; C$_6$-C$_{12}$ cycloalkyl or alkylcycloalkyl;
the radicals R$_7$, which can be the same or different, are: H; C$_1$-C$_8$ alkyl; C$_2$-C$_6$ alkenyl; C$_6$-C$_{12}$ cycloalkyl or alkylcycloalkyl; C$_1$-C$_4$ hydroxyalkyl; or the group:

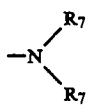

is replaced by a heterocyclic radical bound to the alkyl chain by the nitrogen atom and possibly containing a further heteroatom; or in general formula (I) at least one of the groups:

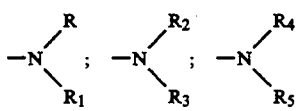

is replaced by a heterocyclic radical bound to the triazine ring by the nitrogen atom and possibly containing a further heteroatom, the other radicals from R to $R_5$, which can be the same or different, have the aforesaid meaning or are: H; $C_1$–$C_{18}$ alkyl; $C_2$–$C_8$ alkenyl; $C_6$–$C_{16}$ cycloalkyl or alkylcycloalkyl, possibly substituted with a hydroxyl or $C_1$–$C_4$ hydroxyalkyl function.

2. Salts of triazine compounds with cyanuric acid as claimed in claim 1, wherein at least one of the groups:

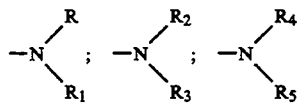

in formula (I) is replaced by heterocyclic radicals: aziridine; pyrrolidine; piperidine; morpholine; thiomorpholine; piperazine; 4-methylpiperazine; 4-ethylpiperazine; 2-methyl-piperazine; 2,5-dimethylpiperazine; 2,3,5,6-tetramethylpiperazine; 2,2,5,5-tetramethylpiperazine; 2-ethylpiperazine; or 2,5-diethyl-piperazine.

3. Salts of triazine compounds with cyanuric acid as claimed in claim 1 or 2, wherein the group:

is replaced by a heterocyclic radical: aziridine; pyrrolidine; piperidine; morpholine; thiomorpholine; piperazine; or 4-methylpiperazine; 4-ethylpiperazine.

* * * * *

UNITED STATES PATENT AND TRADEMARK OFFICE
CERTIFICATE OF CORRECTION

PATENT NO.   : 5,371,218
DATED        : December 6, 1994
INVENTOR(S)  : Roberto CIPOLLI, et al.

It is certified that error appears in the above-indentified patent and that said Letters Patent is hereby corrected as shown below:

On the title page, Item [73], the Assignee should read:

--Ministero dell'Universita' e della Ricerca Scientifica e
  Tecnologica--

Signed and Sealed this

Second Day of May, 1995

Attest:

BRUCE LEHMAN

*Attesting Officer*           *Commissioner of Patents and Trademarks*